(12) United States Patent
Powers et al.

(10) Patent No.: US 6,750,006 B2
(45) Date of Patent: Jun. 15, 2004

(54) METHOD FOR DETECTING THE PRESENCE OF MICROBES AND DETERMINING THEIR PHYSIOLOGICAL STATUS

(75) Inventors: Linda S. Powers, Logan, UT (US); Christopher R. Lloyd, North Logan, UT (US)

(73) Assignee: Microbiosystems, Limited Partnership, Cheyenne, WY (US)

( * ) Notice: Subject to any disclaimer, the term of this patent is extended or adjusted under 35 U.S.C. 154(b) by 0 days.

(21) Appl. No.: 10/054,419

(22) Filed: Jan. 22, 2002

(65) Prior Publication Data

US 2003/0138875 A1 Jul. 24, 2003

(51) Int. Cl.[7] .............................. C12Q 1/00; C12P 35/06
(52) U.S. Cl. .............................................. 435/4; 435/49
(58) Field of Search .................... 435/5, 4, 29

(56) References Cited

U.S. PATENT DOCUMENTS

| | | |
|---|---|---|
| 3,850,525 A | 11/1974 | Kaye |
| 4,745,285 A | 5/1988 | Recktenwald et al. |
| 4,900,934 A | 2/1990 | Peeters et al. |
| 5,208,651 A | 5/1993 | Buican |
| 5,294,799 A | 3/1994 | Aslund et al. |
| 5,418,371 A | 5/1995 | Aslund et al. |
| 5,424,959 A | 6/1995 | Reyes et al. |
| 5,474,910 A | 12/1995 | Alfano |
| 5,491,343 A | 2/1996 | Brooker |
| 5,701,012 A | 12/1997 | Ho |
| 5,760,406 A | 6/1998 | Powers |
| 5,866,430 A | 2/1999 | Grow |
| 5,968,766 A | 10/1999 | Powers |
| 6,124,597 A | 9/2000 | Shehada et al. |
| 6,139,800 A | 10/2000 | Chandler |

OTHER PUBLICATIONS

Hill et al., "Ultraviolet Fluorescence Imaging Applications", Journal of Process Analytical Chemistry 5 (3,4) : 108–114 (2000).*

* cited by examiner

Primary Examiner—Sandra Saucier
(74) Attorney, Agent, or Firm—K. S. Cornaby (57) ABSTRACT

Method and apparatus for the detection of microbes in liquids, in air and on non-living surfaces in which samples are exposed to electromagnetic radiation of specific energies capable of exciting various metabolites, cofactors and cellular and spore components, with the microbial cells to be sampled (and more specifically the excited metabolites, cofactors and or other cellular components) contained therein emit fluorescence that can be measured. The signal from the background and scattered excitation signals is removed from the fluorescence signals of the microbial components, the relative fluorescent signals of the intrinsic microbial components are required to lie within physiological ranges, and the amplitude of the background-corrected fluorescence signals used to enumerate the microbe content in the sample.

24 Claims, 6 Drawing Sheets

METHOD FOR DETECTING THE PRESENCE OF MICROBES AND DETERMINING THEIR PHYSIOLOGICAL STATUS

This invention relates to a method and apparatus for sensing the presence of microbes (bacteria, fungi, protozoa, rickettsiae and or other microorganisms) and spores on non-living surfaces, in air and in liquids.

BACKGROUND OF THE INVENTION

It is of course elementary that all microbial cells produce energy for their cellular activity through respiration. As cellular respiration occurs in living cells, pyridine nucleotides are reduced, flavins are oxidized, and other coenzymes and metabolites are produced. Alternatively, spores are found to be abundant with a calcium dipicolinic acid complex (a fluorescent compound otherwise rare in nature). The oxidation state of pyridine nucleotides, flavins and other cofactors, and/or the presence of calcium dipicolinate, can be simultaneously elucidated by concurrent excitation of each component with the appropriate electromagnetic radiation followed by detection of the characteristic radiation emitted by these individual fluorophores. Simultaneous excitation of a sample with multiple energies characteristic of the excitation for fluorescent cellular and endospore components with the subsequent collection and detection of emitted and reflected/scattered light energies (both associated with and independent of the fluorophores, respectively) is fundamental for the detection of microbes in a sample or on a non-living surface by the method described herein.

The detection of respiring cells in real world samples is made more reliable by the aforementioned method for two reasons. First, the simultaneous excitation of microbes by multiple excitation energies and ensuing coincident detection of numerous fluorescence signals reduces the chance of interference, as the probability of an interference source duplicating the characteristics of numerous fluorophores is extremely small. Second, the relative quantities of the intrinsic metabolites, and thus of the resulting fluorescent signals, have been found to fall within defined physiological ranges. Analysis of the signals is achieved with a method capable of two things: (1) separating the detected fluorescent signals originating from any microbes present from interferences or background signals and or scattered excitation signals, and (2) a requirement that the intensities of the signals from microbial metabolites, microbial components and spore components fall within physiological ranges. Thus, the basis for the detection of microbes in a sample is comprised of the following steps: first, excitation of a sample simultaneously with multiple excitation energies characteristic of cellular metabolites, microbial components, and spore components; second, the subsequent collection of the numerous individual fluorescence signals (associated with the maxima and minima of the emissions of these excited metabolites); and finally, analysis of the collected signals with a method capable of removing background fluorescence and comparing the relative signal magnitudes of metabolites to known physiological ranges.

Long-established technologies and methods used for microbial detection rely upon detection of products resulting from metabolic reactions, immunological capture or the amplification of expected nucleotide sequences. Since this invention employs detection of multiple intrinsic fluorophores from microbes, coupled with an analysis of the relative amount of signals due to these fluorophores, it can not only determine the presence of microbes, but is also capable of differentiating between viable cells, non-viable cells and spores. This method and apparatus uses no reagents, requires no physical contact with the sample, and delivers 'real-time' results.

There are other microbial detection methods that utilize fluorescence. Many of the flow cytometry methodologies rely on the fluorescence of dye molecules conjugated to immunological proteins targeted to the analyte of interest. An example of this can be found in U.S. Pat. No. 4,745,285 (to Recktenwald, et al.). Other fluorescence methods use added fluorescent metabolic dyes or dye conjugates (as in U.S. Pat. No. 4,900,934 to Peeters, et al.).

Some of the fluorescence-based microbe detection methodologies utilize intrinsic cellular fluorophores. One method (U.S. Pat. No. 5,424,959 to Reyes, et al.) simply compares the fluorescence spectra of the sample with a library of spectra. The method described in U.S. Pat. No. 5,474,910 to Alfano, compares the fluorescence of a sample surface to that of a clean surface. A popular intrinsic fluorophore used in microbial detection methods is the reduced pyridine nucleotide NADH. In U.S. Pat. No. 5,701,012 to Ho, NADH fluorescence is detected in a forced airstream containing the sample and compared to a blank. Alternatively, the ratio of NADH fluorescence to either the scattered excitation signal or other fluorescence emissions is used in U.S. patents to Powers (U.S. Pat. Nos. 5,760,406 and 5,968,766).

In U.S. Pat. Nos. 5,760,406 and 5,968,766, which issued Jun. 02, 1998 and Oct. 19, 1999, respectively, and which are incorporated herein by reference, there is disclosed a method and apparatus for the detection of microbes on non-living surfaces and samples. The sample to be examined is excited with electromagnetic radiation (1) having a wavelength greater than 350 nm causing the excitation of pyridine nucleotides present in microbial cells, and (2) having a wavelength below 340 nm as a measure of other characteristics of the environment. The ratios of the microbial pyridine nucleotide fluorescence emission (resultant from the excitation at the different wavelengths) to the reflected excitation signals are calculated and compared, as the basis for both the detection and quantitation of microbes present on the sample. This invention is able to locate and quantitate microbes on non-living surfaces, including meats.

Whereas the aforementioned patents to Powers depend upon ratio fluorescence for the detection of a single metabolite, the present invention utilizes excitation of one or more fluorophores coupled with an algorithm that subtracts the detected signals due to the scattered/reflected excitation energies. This difference in design and methodology makes the current invention better able to detect and quantitate microbes on non-living surfaces, in liquids and in air relative to other fluorescence methods. The current invention is superior in its detection of microbes as the detection of multiple intrinsic fluorophores reduces the probability of false positive results due to background interferences. The detection of microbes with the foregoing method and apparatus will have uses in biowarfare agent detection, cell sorting, medical diagnostics, sterilization verification, water quality testing, food production and preparation safety, and emergency response teams tasked with the detection, decontamination and protection of public infrastructure facilities.

With recent announcements of bacterial contamination in foodstuffs (meats, poultry, seafood, juices, fruits and vegetables), there has been a need to provide a method and apparatus that can be used to detect such microbial contamination in foods, on foods and on food preparation surfaces.

This method and apparatus, as an object of the invention, should be operated inexpensively and rapidly in, for example, meat and poultry production facilities.

It is yet another object of the invention to provide a method and apparatus for use in the detection of microbial contamination on foods in which the fluorescence of pyridine nucleotides, flavins and other cofactors and spore components are excited by electromagnetic radiation to distinguish the metabolic reactions and spore components of microbes from the tissue of foodstuffs, allowing microbial contamination on foods to be determined without contact with said food.

It is accordingly an object of the invention to provide a method and apparatus that can be used in the detection of microbial contamination on non-living surfaces, in liquids and air. As a specific object of the invention, the method and apparatus can be used to find microbes and microbial contamination inexpensively and rapidly in, for example, health-care facilities, research laboratories, water treatment and testing stations, public buildings and on the battlefield.

It is yet another object of the invention to provide a method and apparatus for use in the detection of microbial contamination on non-living surfaces and in liquid and air samples in which the fluorescence of pyridine nucleotides, flavins and other cofactors and spore components are excited by electromagnetic radiation to distinguish the metabolic reactions of microbes and/or presence of spores from the background of the media or scattering, allowing microbial contamination in samples to be determined without contact with said sample.

It is yet another object of the invention to provide a method and apparatus for use in the differentiation between viable cells, non-viable cells, spores and non-contaminated samples in which the fluorescence of pyridine nucleotides, flavins and other cofactors and spore components are excited by electromagnetic radiation with the differences in the relative quantities of the intrinsic fluorophores in each used to distinguish the presence of microbes from the background of the media or scattering.

SUMMARY OF THE INVENTION

The concepts of the present invention reside in a method and apparatus for the detection of microbes in which samples are exposed to electromagnetic radiation of numerous specific energies capable of exciting fluorescence from various metabolites, cofactors and cellular and spore components. Thus, the microbial cells and spores to be sampled (and more specifically the excited metabolites, cofactors and/or other cellular, viral and/or spore components) contained therein emit fluorescence that can be measured. The collected fluorescence signals (associated with the minima and/or maxima of the signals emitted from the cellular/viral/spore components) are analyzed with a method capable of (1) removing any background or reflected/scattered excitation signal, and (2) comparing the relative fluorescent signals of metabolites, cofactors and spore components to known physiological ranges.

Thus, the method and apparatus of the present invention provides an inexpensive and rapid way in which to scan samples to detect and quantitate the presence of microbial contamination without contact with the sample. Being able to evaluate microbial contamination in a sample without contact reduces the risk of introducing contamination.

In accordance with this form of the invention, it is frequently desirable to utilize light source(s) emitting electromagnetic radiation above 200 nm. In accordance with the present form of the invention, the light emitted by the light source is specific to or filtered to pass there through electromagnetic radiation of energies specific to excite pyridine nucleotides, flavins, porphyrins, cofactors and/or calcium dipicolinate.

In accordance with another embodiment of the invention, it is possible, and sometimes desirable, to direct electromagnetic radiation of ultraviolet energies (wavelengths between 200 and 300 nm) at the sample. The ultraviolet light excites aromatic amino acids and nucleic acids, some of whose emission is self-absorbed by the sample sequentially exciting calcium dipicolinate and pyridine nucleotides, some of whose emission is self-absorbed by the sample in turn exciting cofactors (e.g., flavins), part of whose emission is used to excite porphyrins and other flavins. The fluorescent emissions of the sample are collected and analyzed as described previously. The use of ultraviolet light results in a relatively shallow sampling penetration depth of a sample.

In accordance with another embodiment of the invention, it is possible, and sometimes desirable, to direct electromagnetic radiation of energies capable of exciting specific metabolites, cofactors and cellular/spore components and also energies that do not interact with the microbes. Thus, in accordance with this embodiment of the invention, the resulting fluorescent signal emanating from the sample (both from the microbial components and those simply reflected/ scattered from the sample) can be measured and the presence of microbes determined by comparing the ratios of the emitted signals from the microbes compared to those reflected/scattered from the sample.

In accordance with the practice of the invention, a sensor is used to detect not only the fluorescence generated by the intrinsic fluorophores but also to detect the reflected or scattered electromagnetic radiation. This serves to normalize the signal and compensate for variations in the signal that might otherwise be caused by the use of varying distances between a probe and the sample being scanned and variations between different samples or surfaces.

It has also been found that by rapidly changing the electromagnetic radiation directed to the sample at frequencies different than 60 Hertz, the effects of ambient light (and particularly fluorescent light) can be substantially minimized. The modulation of the excitation energy also permits the sensor to be moved to direct the electromagnetic radiation to various parts of a sample without substantially affecting the accuracy of the measurement of the microbial content.

Most commercially available microbe detectors rely on the growth of microbial cultures to obtain sufficiently large samples (outgrowth) for the subsequent application of differential metabolic tests for species (genus) identification. However, techniques requiring bacterial outgrowth may fail to detect viable but nonculturable cells. Conversely, the growth media employed may favor the growth of bacteria with specific phenotypes.

Other approaches to microbial detection depend upon the immunological capture of either the microbes themselves or their components. The most popular immunoassay method, enzyme-linked immunosorbent assay (ELISA), has a best detection limit of several hundred cells. (This is well below the $ID_{50}$ of extremely infectious bacteria such as *Shigella flexneri*.) These techniques likewise involve significant problems because the antibodies employed are very sensitive to variations in pH, ionic strength and temperature. Antibodies directed to microbial components not only are relatively expensive to develop and produce, but are also susceptible to degradation by a host of proteolytic enzymes in 'dirty' samples. In addition, the density of antibody molecules supported on surfaces (e.g., microwell plates or magnetic beads) is not as high as is frequently necessary.

More sensitive but less rapid typing schemes utilize the polymerase chain reaction (PCR) for amplification of bacterial DNA or RNA, followed by nucleic acid sequencing to detect the presence of a particular bacterial species. Such general amplification and sequencing techniques require technical expertise and are not easily adaptable outside of specialized laboratory conditions. PCR-based techniques utilize the inference of microbial presence, since these techniques provide only a positive analysis for an intact target nucleic acid sequences, not necessarily microbes. Moreover, the detection of specific microorganisms in environmental samples is made difficult by the presence of materials that interfere with the effectual amplification of target DNA in 'dirty' or real-world samples.

Mass spectral analysis of volatile cell components (e.g., fatty acids) after sample lysis or pyrolysis has been used for the detection of bacteria and viruses. Unfortunately, identification of the analyte is unreliable as the compositions of a microbe's volatile components change depending upon different environmental growth conditions.

Immunological, mass spectral and PCR-based methods are all unable to ascertain if microbes in the sample were viable. Immunological and PCR-based methods both use relatively expensive reagents that require special handling. The microbial detection method and apparatus described herein is able to determine the viability of detected bacteria, fungi, protozoa, and rickettsiae. The method and apparatus requires no reagents, no contact with the sample, inexpensive to perform and delivers 'real-time' results. These, and other objects, features and advantages of the present invention will become apparent upon review of the following detailed descriptions of the disclosed embodiments and the appended claims.

DETAILED DESCRIPTION OF THE INVENTION

Figure 1:
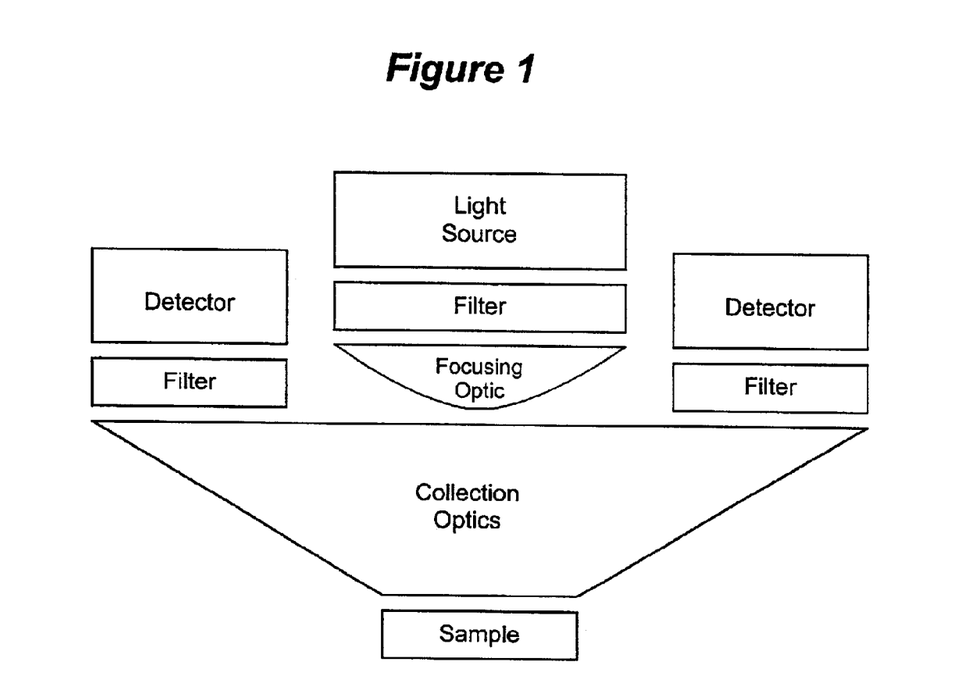
FIG. 1 is a block diagram of the most basic features of the invention.

The basic elements for the apparatus described by this invention are shown as a block diagram in FIG. 1. The apparatus consists of a light source, excitation filters, focusing optics, collection optics, emission filters and detectors. Electromagnetic radiation is directed from the light source towards the sample, passing through the excitation filters and focusing optics if necessary, to excite the intrinsic fluorophores in the sample. The scattered and reflected excitation radiation, along with the emitted fluorescence radiation, are collected with the collection optics and directed towards the detectors. Emission filters ensure that only the energies of interest are measured.

Various embodiments of the invention, including different configurations and utilizing diverse components, are possible. The fundamental components for this microbial detection method permit: the excitation of multiple intrinsic microbial fluorophores, collection and detection of emitted and reflected/scattered light energies, and analysis of the detected signals with a method that is able to correct for background interferences and compare the relative signal strengths to known physiological parameters. The configuration and components employed in any apparatus using this method should be matched with the application requirements and expected interferences.

It is possible, and sometimes desirable, to utilize a light source that provides a broad band illumination. The kind of light source employed is influenced by its ability to produce electromagnetic radiation of the wavelengths required to excite the intrinsic microbial components of interest. Additionally, it is sometimes desirable to use a pulsed light source allowing measurement of the environmental background during the off cycle. The light sources that can be used include lamps with various bulbs (e.g., mercury, tungsten, deuterium, xenon), light emitting diodes (LEDs), and diode lasers specific for the required excitation energies. The kind of light source used depends upon the intensity of excitation radiation needed and detection limit required.

The excitation and emission filters used in the various embodiments of the invention include interference filters, impregnated glass, series of cutoff filters, gelatin filters, monochromaters, gratings and the like. The light cutoff characteristics of the emission filters used depend on how much of the scattered and reflected excitation radiation signal can be tolerated by the analysis method or what detection limit is required. If light sources having only the energies of interest are employed, the excitation filters may not be necessary; if the light source is collimated (such as a laser) then the focusing optic may not be required. (The purpose of the focusing optic is to direct the excitation radiation to the sampling area or volume.) It is important to note that with multi-photon excitation it is possible to use light sources with energies less than the excitation energies of the fluorophores of interest.

The purpose of the collection optics is to deliver the light emitted from the excited microbial fluorophores and that scattered and reflected from the sample to the detectors. If interference filters are utilized to discriminate these emission energies, then the collected light needs to be collimated for these filters to work optimally. Fiberoptic cables can also be used to both deliver the excitation radiation to the sample and to collect the emitted radiation and direct it towards the detectors. It is possible, and sometimes desirable, to utilize polished metal reflective, sapphire, fused silica, quartz, $MgF_2$, and or $CaF_2$ optical components as many optical components exhibit fluorescence in the ultraviolet and visible range.

The detectors are used to convert the emitted electromagnetic radiation into an electrical signal that can be measured. Numerous detectors, with different sensitivities, can be utilized in the embodiments of the invention: photomultiplier tubes (PMTs), avalanche photodiodes (APDs), pin diodes, CCDs, and the like. The detector chosen would depend upon the energy of the radiation to be detected, the strength of the emission signal, and the required detection limit of the apparatus.

Figure 2:
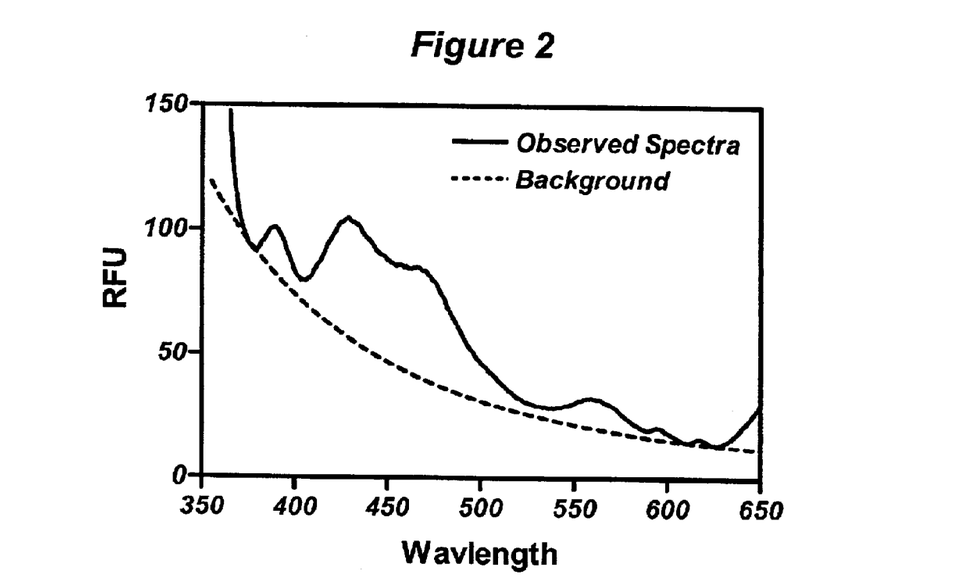
FIG. 2 shows the emission spectra of a solution of bacteria (*Bacillus thuringiensis*) in low fluorescing media when excited with radiation of 345 nm. The solid line shows the emission spectra of the bacteria and the dashed line indicates the contribution of the Rayleigh scattering to this spectra.

The collected emission energies, having been converted to amplified electrical signals, are analyzed with a method capable of removing any background fluorescence and scattered excitation contributions. The choice of excitation and emission energies used in a specific embodiment depends upon the target microbes and their expected physiological status. Table 1 lists the excitation and emission ranges of some of the more abundant intrinsic fluorescent compounds found in various microbes (and proteinaceous toxins) and indicates their likely presence in each. (Proteinaceous microbial toxins can be detected using this method and apparatus in a manner similar to that used for the detection of viruses.)

emission spectrum of the bacterial solution when excited with 325 nm, 345 nm and 570 nm shows minima near 515 nm and 850 nm. The measured fluorescence intensities at 515 nm and 850 nm are used to calculate the unknown values of A and C from the aforementioned equation, ultimately allowing for the subtraction of the background signal from the detected signal. Ralyleigh scattering background subtraction is particularly suited for liquid and air samples; other sample media exhibit different backgrounds and can be treated with the appropriate methods (e.g., Mie scattering, etc.).

Figure 3:
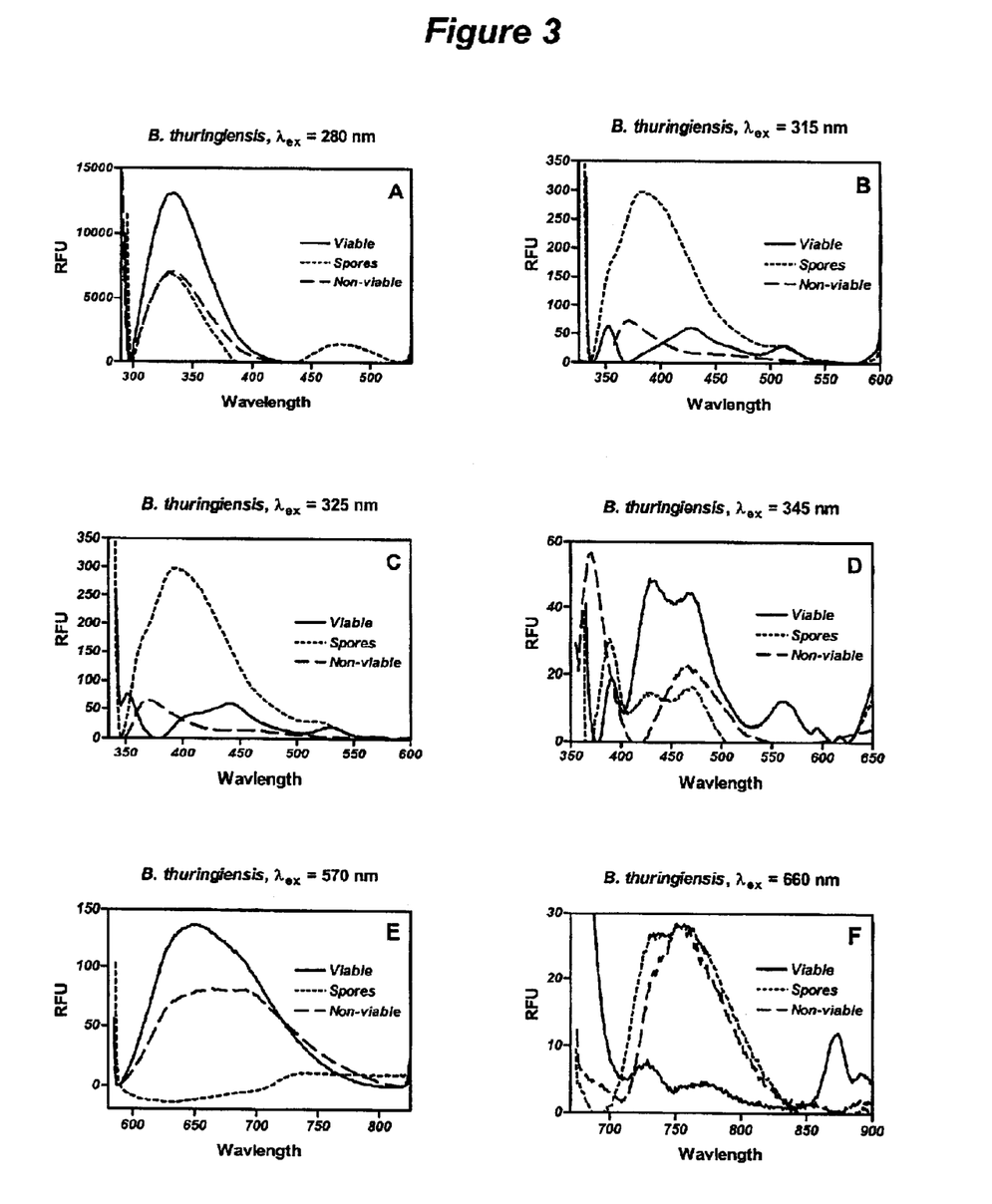
FIG. 3 shows the emission spectra of viable cell, non-viable cell and spore (*Bacillus thuringiensis*) solutions due to the various intrinsic fluorophores excited at different wavelengths (after background subtraction).
Figure 4:
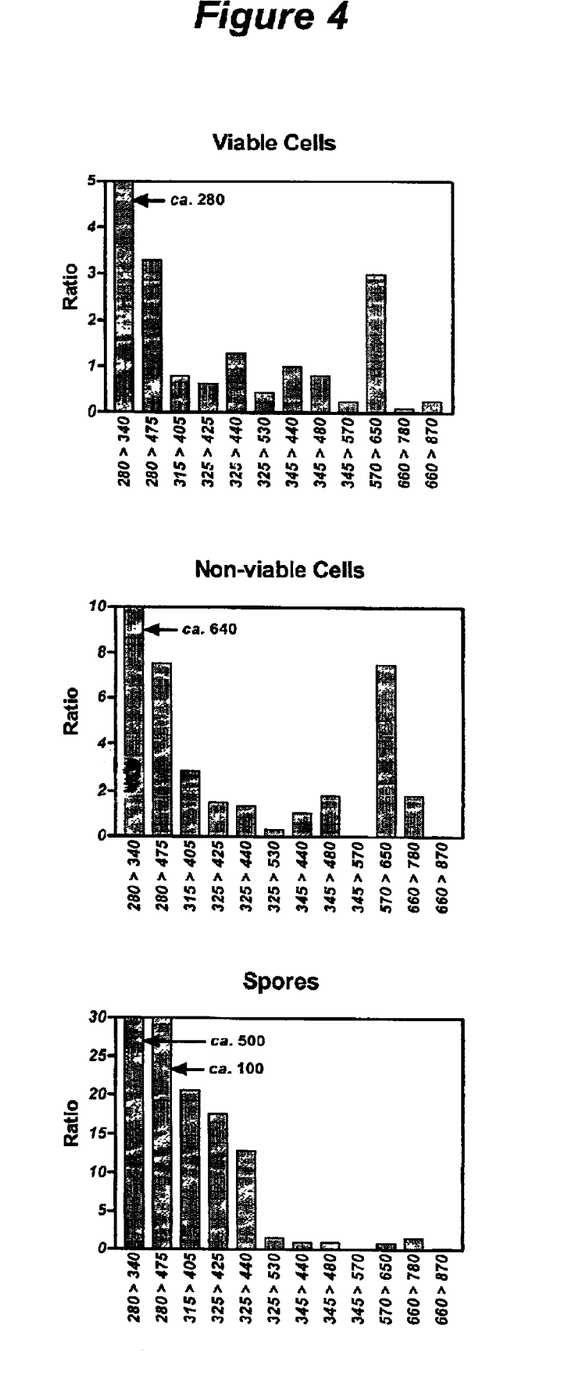
FIG. 4 shows the distribution differences of the fluorescence signals (normalized to the emission at 440 nm after background subtraction) between viable cells, non-viable cells and spores of *Bacillus thuringiensis* in solution.

FIG. 3 shows the background-subtracted emission spectra of viable bacteria, non-viable bacteria and spore solutions (*Bacillus thuringiensis*) due to the various intrinsic fluorophores excited at 280 nm (A), 315 nm (B), 325 nm (C), 345 nm (D), 570 nm (E) and 660 nm (F). FIG. 4 shows the obvious differences of the fluorescence signals (normalized to the emission at 440 nm after background subtraction) between said viable cell (A), non-viable cell (B) and the spore (C) solutions. The analysis method uses these differences between the viable cells, non-viable cells and spore solutions to distinguish between these in samples. The magnitudes of the detected and background-subtracted signals are used to quantitate the number of microbes in the sample.

In the one embodiment of the invention, the use of excitation filters at 325 nm, 345 nm and 570 nm would allow for the detection of and discrimination between live cells, dead cells and spores. These excitation filters would allow the excitation of reduced pyridine nucleotides, various

TABLE I

Excitation and Emission Ranges for Microbial Fluorophores.

| Excitation Range (nm) | Emission Range (nm) | Fluorophore | Viable Cells | Non-viable Cells | Spores | Viruses | Toxins |
|---|---|---|---|---|---|---|---|
| 260–285 | 340–360 | Nucleic Acids | X | X | X | X | |
| 265–280 | 340–360 | Tryptophan | X | X | X | X | X |
| 265–280 | 340–360 | Tyrosine | X | X | X | X | X |
| 270–280 | 380–400 | ATP | X | | | | |
| 270–290 | 460–480 | Ca-Dipic | | | X | | |
| 310–330 | 400–430 | Ca-Dipic | | | X | | |
| 320–330 | 430–450 | RPN | X | | | | |
| 340–365 | 430–450 | RPN | X | | | | |
| 340–360 | 470–490 | RPN | X | | | | |
| 430–450 | 520–535 | Flavins | X | | | | |
| 470–485 | 560–580 | Flavins | X | | | | |
| 560–585 | 615–680 | Porphyrins | X | X | | | |
| 560–580 | 620–700 | Flavins | X | X | | | |
| 610–650 | 750–800 | Unknown | | X | X | | |
| 650–670 | 730–780 | Unknown | | X | X | | |

(In Table 1, ATP is adenosine triphosphate and RPN refers to the reduced pyridine nucleotides.)

FIG. 2 shows the emission spectra of a bacterial solution (*Bacillus thuringiensis*) in a minimally fluorescing media when excited with light at 345 nm. The solid line shows the observed emission spectra of the bacteria and the dashed line indicates the contribution of the Rayleigh scattering to this spectra. Subtraction of the Rayleigh background from the observed spectra results in the true emission spectra due to the metabolites excited by 345 nm light (FIG. 3D). The magnitude of the background from Rayleigh scattering at wavelength $\lambda$ can be described by the equation: $I = A/\lambda^4 + C$. (In this equation, I is the intensity of the incident light; A is determined by the experimental conditions; the value for the constant C is typically determined by the characteristics of the instrument used to collect the data.) The combined flavins, calcium dipicolinate, hemoproteins and other components. The selection of filters for the emission detection of the excited fluorophores would include those at 405 nm, 440 nm, 480 nm and 650 nm; these filters correspond to maxima in the emission spectra of the excited flurophores. Additionally, other emission filters (545 nm and 850 nm) allow for the determination of the magnitude of the reflected scattered background. To achieve a low detection limit, the following configuration was constructed. A pulsed xenon lamp was used as the light source with interference excitation filters. A focusing optic is added to collimate the light before the interference filters. The focusing and collection optical pieces were constructed from polished reflective optics to eliminate any background fluorescence. The parabolic collection optics, which collected ca. 90% of the emitted signal, were fitted with interference emission filters, collimating optics and PMTs. The instrument functions, data collection, integration and analysis were controlled by a microcontroller.

Figure 5:
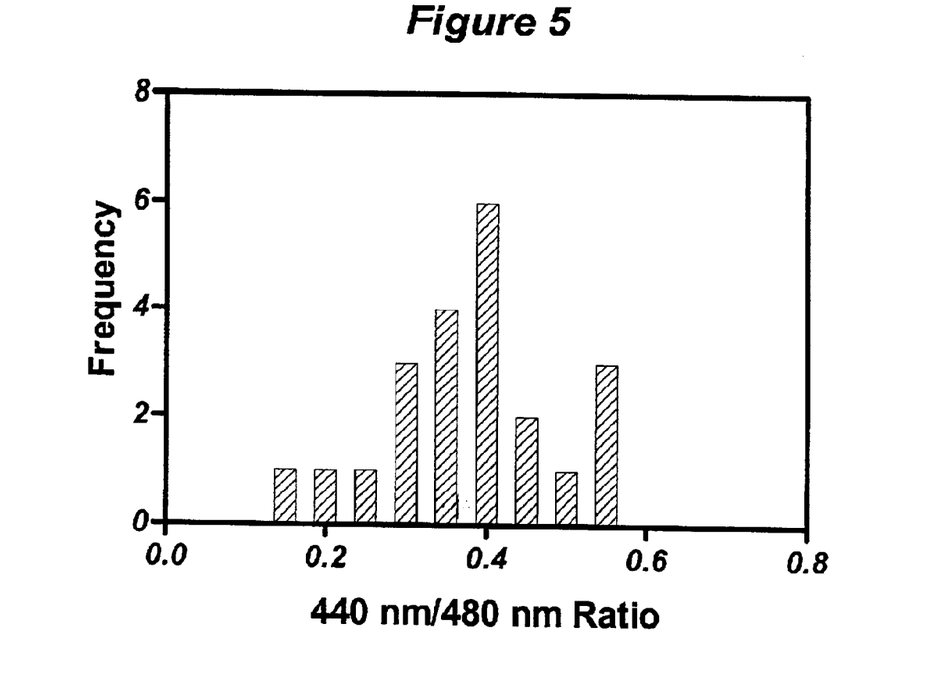
FIG. 5 shows the distribution of the 440 nm to 480 nm fluorescence emission ratios after background subtraction for 22 species of bacteria.

In this embodiment of the invention, the detection method required the relative ratios of the detected and background-corrected signals to lie within certain physiological ranges. Analysis of greater than 500 samples from more than twenty different species of bacteria and spores showed that the numerous ratios could be used to ensure a statistically significant identification. FIG. 5 shows the distribution for just one of these ratios (440 nm/480 nm ratio after background subtraction) of 22 species of bacteria, thus defining the physiological range required for the detection method. The method could also discriminate bacteria-containing solutions from sterile media and other biochemical buffers. Using a variety of methods and the following ratios (650/405, 405/440, 480/440, 650/440, 405/480 and 650/480), e.g., Neyman-Pearson test, fuzzy logic and a trained neural network (utilizing a multilayer perceptron), these gave a 99%, 95.6% and 100% probability of detection, respectively for the presence of bacteria. (False alarm probabilities of the 500 data points taken for these detection algorithms were as follows: Neyman-Pearson (0.01%), fuzzy logic (0%), and neural net (0%).)

Figure 6:
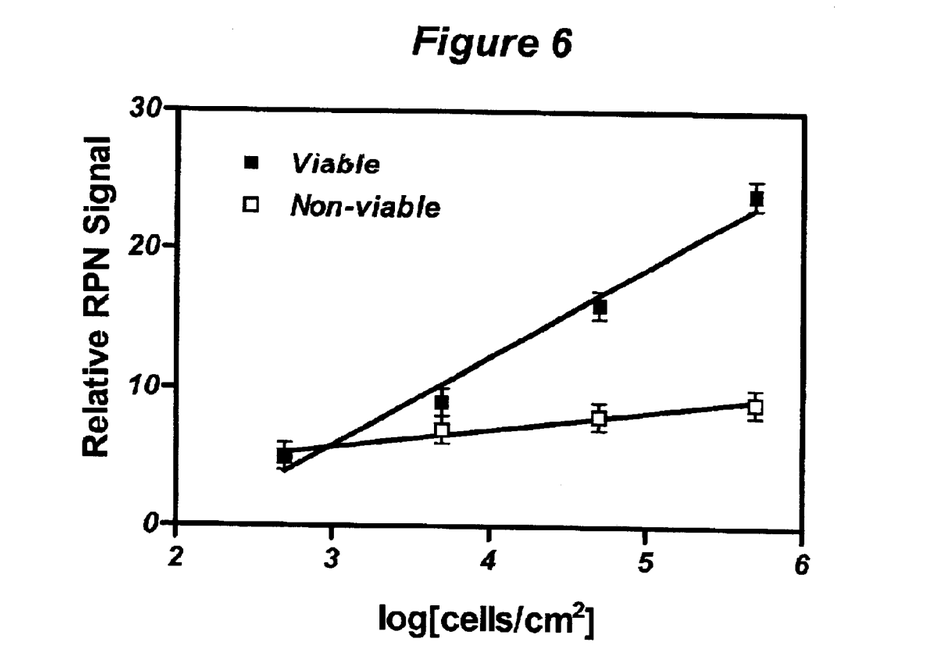
FIG. 6 shows the response of the reduced pyridine nucleotide (RPN) fluorescence emission of one embodiment of the invention to viable and non-viable *Salmonella typhi* cells on a sterile surface.
Figure 7:
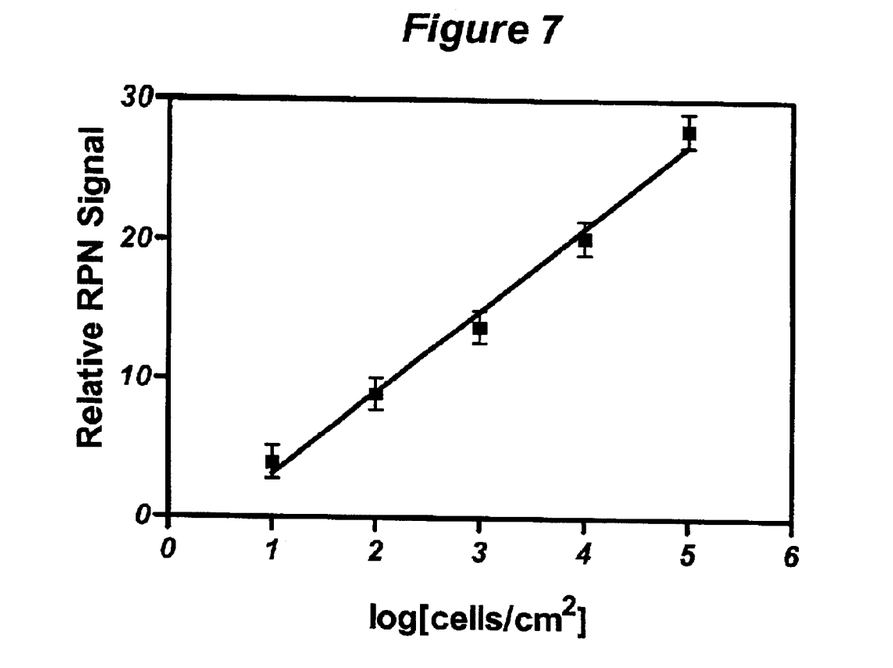
FIG. 7 shows the response of the RPN fluorescence emission of *Escherichia coli* on the surface of turkey.
Figure 8:
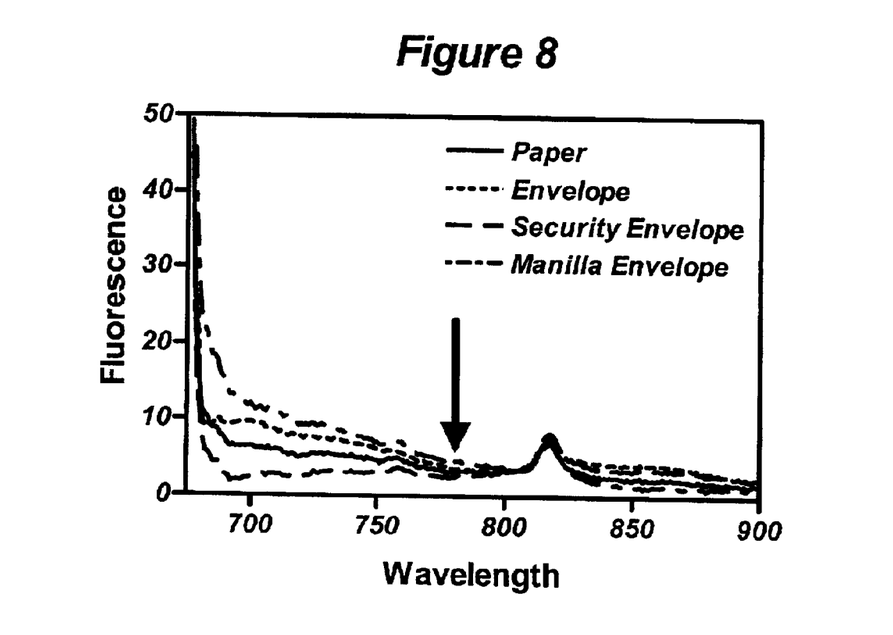
FIG. 8 shows the spectroscopic window in the fluorescence emission spectra of paper and various samples of envelopes.
Figure 9:
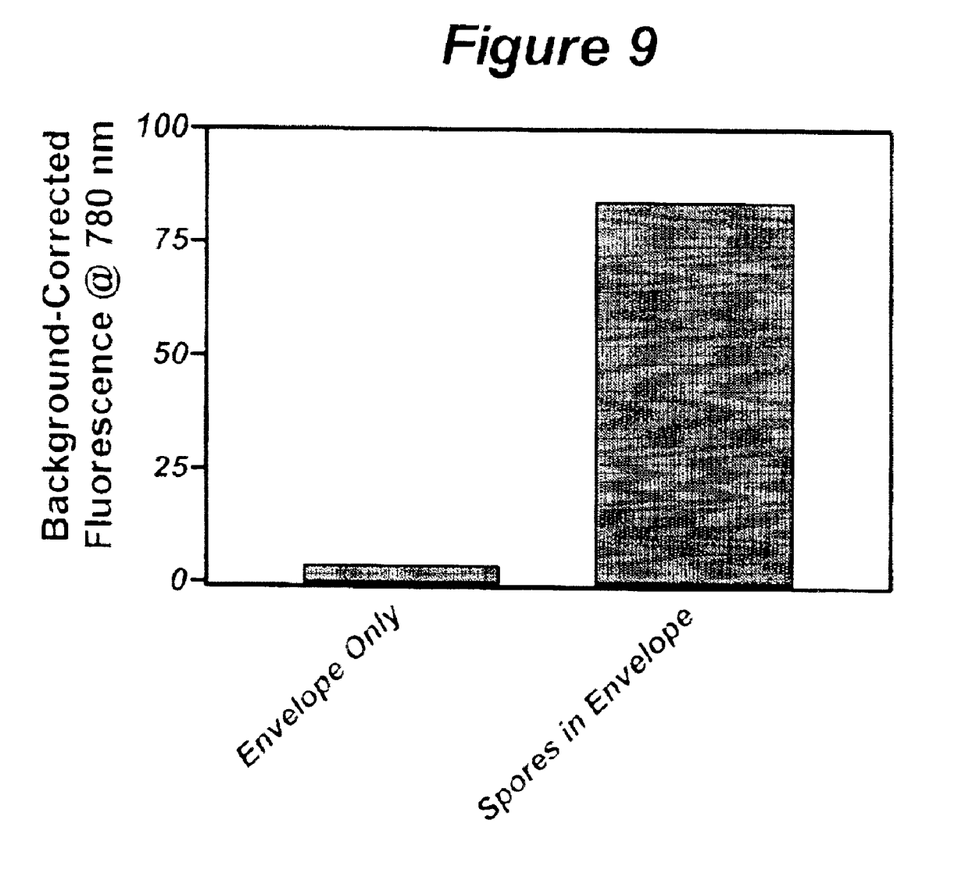
FIG. 9 shows the response of the background-corrected 780 nm fluorescence channel of one embodiment of the invention to several milligrams of *Bacillus thuringiensis* spores in a sealed envelope.

FIG. 6 shows data from one emission (RPN) of the instrument for viable and non-viable *Salmonella typhi* cells on the surface of a glass slide. The difference between viable and non-viable cells in the signal from this fluorescence is clear. FIG. 7 shows the response of the RPN emission to *Escherichia coli* on the surface of turkey. A detection limit well below that observed for other microbial detection methods is observed in real-time, without the need for reagents or touching the meat surface.

In another embodiment of the invention, LEDs centered around 570 and 660 nm are used to excite the component(s) found in spores and dead cells shown in FIGS. 3D and 3F. FIG. 8 shows the emission spectra of paper and various samples of envelopes when excited with light at 660 nm; the arrow in this figure shows the location of the emission expected from spores and non-viable cells at this excitation. As the paper and envelopes contain this spectroscopic window it is possible to detect bacterial endospores behind paper and inside envelopes. It is possible, and sometimes desirable, to include excitation at 570 nm as the resulting emission from non-viable cell component(s) between 610 and 680 nm excites the spore components that fluoresce in the aforementioned spectroscopic window. FIG. 9 shows the differences between the 780 nm background-corrected fluorescence signals of an envelope and a sample of freeze-dried *Bacillus thuringiensis* spores sealed inside of the same envelope. With this embodiment of the invention it is possible to quickly detect spores in envelopes without the need for reagents, sample processing, contact with the sample or opening the envelope.

The embodiments of the present invention described above are intended to be merely exemplary, with other configurations, variations and modifications utilizing the fore mentioned basic ideas available to those skilled in the art without departing from the spirit of the invention. The scope of this method and apparatus to detect microbes includes utilization of simultaneous excitation of multiple intrinsic microbial fluorophores with subsequent analysis of the detected emissions with methods that concurrently account for background signals and require said signals to lie within physiological ranges. All variations, modifications and configurations are intended to be within the scope of the present invention as defined in the appended claims.

What is claimed:

1. A method for the detection and enumeration of microbes comprising:

a. exciting at least one intrinsic microbial fluorophore having a specific excitation range of electromagnetic radiation wavelength above 200 nm; whereby said intrinsic fluorophore in the microbes is excited to emit fluorescence; and b. detecting the signal intensities associated with the minima and maxima of the microbial fluorescence; and c. detecting the background intensities at the minima and maxima of the microbial fluorescence in the absence of excitation; and d. calculating the intensities of the reflectance and scattering at the maxima of the microbial fluorescence from the intensities of the background-subtracted minima with an appropriate algorithm; and e. subtracting the calculated reflected and scattered signal intensities and measured background intensities from the detected signals of the microbial fluorescence; thereby determining the number of microbes by the magnitude of the detected fluorescence from which background, reflectance, and scattering contributions have been subtracted.

2. The method as set forth in claim 1, wherein the ratios of multiple fluorescence signal intensities, from which measured background and calculated reflectance and scattering have been subtracted, are determined; whereby the detection of the physiological state of the microbes depends upon the requirement that the ratios of the background, scattering, and reflectance-corrected fluorescence signals lie within specified physiological ranges and that the enumeration of the microbes is determined by the magnitude of said detected signals the ratios of which lie within said expected ranges.

3. The method as set forth in claim 1, wherein said microbial fluorophores are selected from the group consisting of nucleic acid polymers, tryptophan-containing proteins, tyrosine-containing proteins, adenosine triphosphate, calcium dipicolinate, reduced pyridine nucleotides, flavins, porphyrin-containing proteins, and other components excited in the 610–670 nm region.

4. The method of claim 1, wherein the viable microbes to be detected include at least one of the following: bacteria, fungi, protozoa, and rickettsiae; and the intrinsic microbial fluorophores used to detect the microbes include at least one of the following: nucleic acid polymers, tyrosine-containing proteins, tryptophan-containing proteins, adenosine triphosphate, reduced pyridine nucleotides, flavins, porphyrin-containing proteins, and others excited in the 610–670 nm region.

5. The method of claim 1, wherein non-viable microbes to be detected include at least one of the following: bacteria, fungi, protozoa, and rickettsiae; and the intrinsic microbial fluorophores used to detect the microbes include at least one of the following: nucleic acid polymers, tryptophan-containing proteins, tyrosine-containing proteins, reduced pyridine nucleotides, flavins, porphyrin-containing proteins, and others excited in the 610–670 nm region.

6. The method of claim 1, wherein the microbes to be detected are bacterial endospores and the intrinsic fluorophores used to detect the endospores include at least one of the following: nucleic acid, polymers, tyrosine-containing proteins, tryptophan-containing proteins, calcium dipicolinic acid, and others excited in the 610–670 nm region.

7. The method of claim 1, wherein the microbes to be detected include viruses, and the intrinsic fluorophores used to detect the viruses include at least one of the following: nucleic acid polymers, tyrosine-containing proteins, and tryptophan-containing proteins.

8. A method for the detection and enumeration of microbes comprising:
   a. exciting multiple intrinsic microbial fluorophores with ultraviolet electromagnetic radiation having excitation wavelengths between 200 and 300 nm, whereby intrinsic fluorophores in any microbes present are excited to emit fluorescence, some of which is self-absorbed to excite other microbial fluorophores that in turn emit fluorescence and
   b. detecting the fluorescence signal intensities associated with the minima and maxima of the microbial fluorescence; and
   c. detecting the background intensities at the minima and maxima of the microbial fluorescence in the absence of excitation; and
   d. calculating the intensities of the reflectance and scattering at the maxima of the microbial fluorescence from the intensities of the background-subtracted minima with an appropriate algorithm: and
   e. subtracting the calculated reflected and scattered signal intensities and measured background signal intensities from the detected signals of the microbial fluorescence; and
   f. determining that the ratios of the detected fluorescence signals from which background, reflectance, and scattering contributions have been subtracted lie within physiological ranges, thereby determining the number of microbes by the magnitude of the detected fluorescence signals from which background, reflectance, and scattering contributions have been subtracted the ratios of which lie within physiological ranges.

9. The method as set forth in claim 8, wherein the intrinsic microbial fluorophores of said microbes include one or more of the group consisting of nucleic acid polymers, tryptophan-containing proteins, adenosine triphosphate, and calcium dipicolinate compounds.

10. The method as set forth in claim 8, wherein secondary-excited microbial fluorophores include one or more of the group consisting of calcium dipicolinate, reduced pyridine nucleotides, flavins, porphyrin-containing proteins, cellular components excited in the 610–670 nm region, and the like.

11. The method as set forth in claim 8, wherein the viable microbes to be detected include at least one of the following: bacteria, fungi, protozoa, and rickettsiae, and the intrinsic microbial fluorophores used to detect the microbes are selected from the group consisting of nucleic acid polymers, tyrosine-containing proteins, tryptophan-containing proteins, adenosine triphosphate, reduced pyridine nucleotides, flavins, porphyrin-containing proteins, and cellular components excited in the 610–670 nm region.

12. The method of claim 8, wherein the non-viable microbes to be detected include at least one of the following: bacteria, fungi, protozoa, and rickettsiae; and the intrinsic microbial fluorophores used to detect the microbes are selected from the group consisting of nucleic acid polymers, tyrosine-containing proteins, tryptophan-containing proteins, reduced pyridine nucleotides, flavins, porphyrin-containing proteins, and cellular components excited in the 610–670 nm region.

13. The method of claim 8, wherein the microbes to be detected are bacterial spores and the intrinsic fluorophores used to detect the spores include at least one of the following: nucleic acid polymers, tyrosine-containing proteins, tryptophan-containing proteins, calcium dipicolinic acid, and spore components excited in the 610–670 nm region.

14. A method for the detection and enumeration of microbial proteinaceous toxins comprising:
   a. exciting at least one intrinsic fluorophore having a specific excitation range of electromagnetic radiation wavelength above 200 nm; whereby said fluorophores in the proteinaceous toxin present are excited to emit fluorescence; and
   b. detecting the fluorescence signal intensities associated with the minima and maxima of the excited fluorophores; and
   c. detecting the background intensities at the minima and maxima of the fluorescence in the absence of excitation; and
   d. calculating the intensities of the reflectance and scattering at the maxima of the fluorescence from the intensities of the background-subtracted minima with an appropriate algorithm; and
   e. subtracting the calculated reflected and scattered signal intensities and measured background intensities from the detected signal intensities of the fluorescence; thereby determining the amount of proteinaceous toxin by the magnitude of said detected fluorescence from which background, reflectance, and scattering contributions have been subtracted.

15. The method as set forth in claim 14, wherein said microbe fluorophores are selected from the group consisting of tryptophan-containing proteins and tyrosine-containing proteins.

16. A method for the detection and enumeration of spores and non-viable bacteria comprising:
   a. exciting at least one intrinsic microbial fluorophore having a specific excitation range of electromagnetic radiation wavelengths between 550 and 700 nm; whereby said intrinsic fluorophores present in the spores and non-viable bacteria are excited to emit fluorescence; and
   b. detecting the signal intensities associated with the minima and maxima of the fluorescence; and
   c. detecting the background intensities at the minima and maxima of the fluorophores in the absence of excitation; and
   d. calculating the intensities of the reflectance and scattering at the maxima of the microbial fluorescence from the intensities of the background-subtracted minima with an appropriate algorithm; and
   e. subtracting the calculated, reflected and scattered signal intensities and measured background intensities from the detected signal intensities of the excited microbial fluorescence; thereby enumerating the spores and non-viable bacteria by the magnitude of the detected fluorescence from which background, reflectance, and scattering contributions have been subtracted.

17. The method as set forth in claim 16, wherein the ratios of multiple detected, background-corrected signals are determined; whereby the distinction between spores and non-viable bacteria depends upon the requirement that the ratios of the background-corrected fluorescence signals lie within specified physiological ranges and that the enumeration of spores is determined by the magnitude of said detected signals, the ratios of which lie within said expected ranges.

18. The method claim 16, wherein the intrinsic microbial fluorophores used to detect the non-viable bacteria and bacterial spores are selected from a group including flavins, porphyrin-containing proteins, and other components excited in the 610–670 nm region.

19. The method of claim 16, wherein the non-viable bacteria and bacterial spores are detected on surfaces, inside paper envelopes, through paper, in solution and in aerosols.

20. A method for the detection and enumeration of spores and non-viable bacteria comprising:
   a. excitation of multiple intrinsic microbial fluorophores with electromagnetic radiation having excitation wavelengths between 550 and 640 nm, whereby intrinsic fluorophores in any spores and non-viable bacteria present are excited to emit fluorescence, some of which is self-absorbed to excite other spore fluorophores that in turn emit fluorescence;
   b. detecting the fluorescence signal intensities associated with the minima and maxima of the microbial fluorescence; and
   c. detecting the background intensities at the minima and maxima of the intrinsic fluorophores in the absence of excitation; and
   d. calculating the intensities of the reflectance and scattering at the maxima of the microbial fluorescence from the intensities of the background-subtracted minima with an appropriate algorithm: and
   e. subtracting from the calculated, reflected and scattered signal intensities and measured background signal intensities from the detected signal intensities of the excited microbial fluorescence; and
   f. determining that the ratios of the detected, fluorescence signals from which background, reflectance, and scattering contributions have been subtracted lie within physiological ranges, thereby determining the number of bacterial spores and non-viable bacteria by the magnitude of the detected fluorescence signals from which background, reflectance, and scattering contributions have been subtracted, the ratios of which lie within physiological ranges.

21. The method as set forth in claim 20, wherein the intrinsic microbial fluorophores of said microbes include one or more of the group consisting of flavins, porphyrin-containing proteins, and other components excited in the 610–670 nm region.

22. The method as set forth in claim 20, wherein secondary-excited microbial fluorophores include one or more of the group consisting of intrinsic components excited in the 610–680 nm region, and the like.

23. The method of claim 20, wherein the non-viable bacteria and spores are detected on surfaces, inside paper envelopes, through paper, in solution and in aerosols.

24. The method as set forth in claim 20, wherein the spores and non-viable bacteria are detected inside paper envelopes and the secondary-excited microbial fluorophores are excited by emissions from the excited paper products.

* * * * *